United States Patent

Schacht et al.

[11] 3,956,334
[45] May 11, 1976

[54] 2-METHYL-2-[4-(4-PIPERIDINOPHENYL)-PHENOXY]-PROPIONIC ACID 1-METHYL-4-PIPERIDYL ESTER

[75] Inventors: Erich Schacht; Werner Mehrhof; Herbert Nowak; Zdenek Simane, all of Darmstadt, Germany

[73] Assignee: Merck Patent Gesellschaft mit beschrankter Haftung, Darmstadt, Germany

[22] Filed: June 26, 1974

[21] Appl. No.: 483,408

[30] Foreign Application Priority Data
June 28, 1973 Germany.............................. 2332801

[52] U.S. Cl..................... 260/293.64; 260/293.69; 260/293.72; 260/293.73; 260/293.75; 260/293.76; 260/293.82; 260/293.83; 424/267
[51] Int. Cl.².................................. C07D 211/46
[58] Field of Search ............................. 260/293.64

[56] References Cited
UNITED STATES PATENTS
3,526,632  9/1970  Griot............................. 260/293.82
3,804,839  4/1974  Dahm .............................. 260/309.2

Primary Examiner—Sherman D. Winters
Attorney, Agent, or Firm—Millen, Raptes & White

[57] ABSTRACT

Piperidines of the formula

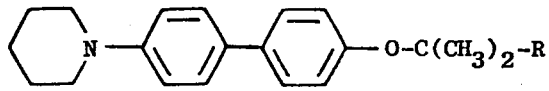

wherein R is —$CH_2OH$, $CO-NR_1R_2$ in which $R_1$ and $R_2$ each are H or alkyl of 1-4 carbon atoms, —$NHCH_2CH_2OH$, —$N(CH_2CH_2OH)_2$, —$NHCH_2CH_2SO_3H$, —$NHNH_2$ or —$NHCH_2COOH$, or —$COOR_3$ in which $R_3$ is 3-pyridylmethyl, 2-acetamidoethyl, 1-methyl-4-piperidyl or 2,3-dihydroxypropyl and the physiologically acceptable salts thereof, have cholesterol-level-lowering and triglyceride-level-lowering activity and can be prepared from 2-methyl-2-[4-(4-piperidinophenyl)-phenoxy]-propionic acid or a functional derivative thereof by reduction or by reaction with a compound of the formula HZ.

2 Claims, No Drawings

2-METHYL-2-[4-(4-PIPERIDINOPHENYL)-PHENOXY]-PROPIONIC ACID 1-METHYL-4-PIPERIDYL ESTER

BACKGROUND OF THE INVENTION

This invention relates to novel N-alkoxyphenylphenyl substituted piperidines.

German application DOS No. 2,112,272 and U.S. Pat. No. 3,804,829 disclose, inter alia, 2-methyl-2-[4-(4-piperidinophenyl)phenoxy]-propionic acids having cholesterol and triglyceride blood level lowering activity. Application Ser. No. 393,936, filed Sept. 4, 1973, claims these compounds.

SUMMARY OF THE INVENTION

The novel compounds of this invention are piperidine derivatives of general Formula I

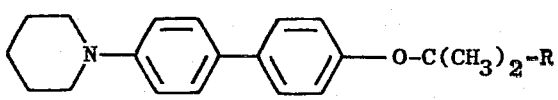

I wherein R is —CH$_2$OH, —CO—Z in which Z is —NR$_1$R$_2$ wherein R$_1$ and R$_2$ is H or alkyl of 1–4 carbon atoms, —NHCH$_2$CH$_2$OH, —N(CH$_2$CH$_2$OH)$_2$, —NHCH$_2$CH$_2$SO$_3$H, —NHNH$_2$ or —NHCH$_2$COOH, or —COOR$_3$, and R$_3$ is 3-pyridylmethyl, 2-acetamidoethyl, 1-methyl-4-piperidyl or 2,3-dihydroxypropyl, and the physiologically acceptable salts thereof with acids or bases.

The compounds of Formula I and the physiologically acceptable salts thereof possess, with a good compatibility, cholesterol-level-lowering and triglyceride-level-lowering activity and can be employed as medicinal agents as well as intermediates for the production of other drugs.

In its process aspect, this invention relates to processes for the production of the novel compounds of this invention.

In its composition aspect, this invention relates to pharmaceutically acceptable compositions comprising a novel compound of this invention.

DETAILED DISCUSSION

The compounds of Formula I are of three general classes, viz.,
a. the alcohol, viz., R is CH$_2$OH;
b. amides and derivatives thereof, viz., R is —CO—Z; and
c. substituted esters, viz., R is —CO—OR$_3$.

The compounds of Formula I and the physiologically acceptable salts thereof with acids or bases, can be produced by a process wherein
a. 2-methyl-2-[4-(4-piperidinophenyl)-phenoxy]-propionic acid (A) or one of the functional derivatives thereof is reacted with a reducing agent or with a compound of the formula HZ and/or with a functional derivative of such a compound; or
b. 4-hydroxy-4'-piperidino-diphenyl is reacted with a compound of Formula II

X—C(CH$_3$)$_2$—R  II wherein X is Hal or an optionally esterified OH-group, Hal being Cl, Br or I, and R has the values given above; or c. a compound of Formula III

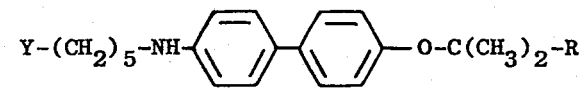

III wherein Y is Hal, NH$_2$ or a free, esterified or etherified OH-group, and R and Hal have the values given above, is treated with a cyclizing agent; or d. a compound of Formula IV

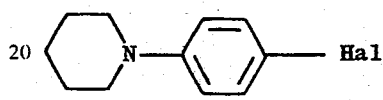

IV wherein Hal has the values given above, is reacted with a compound of Formula V

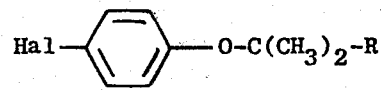

V wherein R and Hal have the values given above, in the presence of a catalyst; or e. a diazonium compound of Formula VI

VI wherein A$^-$ is an anion, is reacted with a compound of Formula VII

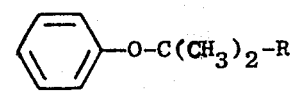

VII wherein R has the values given above; or
f. a compound of Formula VIII

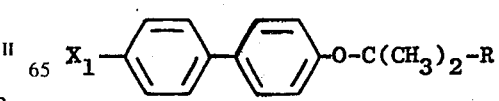

VIII wherein $X_1$ is H, Hal, $NH_2$ or $SO_3M$, and M is an equivalent of a metallic ion, and R has the values given above, is reacted with a compound of Formula IX

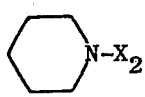 IX wherein $X_2$ is H, M or X, M and X having the values given above, with the provision that $X_1$ and $X_2$ are different and one is H or optionally M;

and optionally thereafter a thus-obtained compound of Formula I is converted by treatment with an acid or a base into the physiologically acceptable acid addition salts and/or metallic salts and/or ammonium salts thereof and/or a compound of Formula I is liberated from one such salt thereof by treatment with a base and/or an acid.

In the above formulae, $R_1$ and $R_2$ preferably are H, methyl, ethyl or isopropyl, but can also be n-propyl, n-butyl, isobutyl, sec.-butyl or tert.-butyl.

X and Y preferably are Cl or Br but can also represent, in addition to free OH and I, for example, alkylsulfonyloxy, preferably 1–6 carbon atoms (e.g., methanesulfonyloxy), arylsulfonyloxy, preferably of 6–10 carbon atoms (e.g., benzenesulfonyloxy, p-toluenesulfonyloxy and 1- and 2-naphthalenesulfonyloxy), and acyloxy, preferably of 1–7 carbon atoms (e.g., acetoxy and benzoyloxy). Moreover, Y can be $NH_2$ or an etherified OH-group, in particular, of 1–7 carbon atoms, e.g., methoxy and other alkoxy and readily cleavable ether groups, e.g., tetrahydropyranyl-2-oxy and benzyloxy.

$A^-$ can be any desired anion and preferably is chloride, bromide, sulfate or acetate.

M is preferably an alkali metal ion, especially a sodium or potassium.

The methods described above for the production of the compounds of Formula I are known per se and described in the literature.

As stated above, these compounds are obtainable, for example, by treatment of 2-methyl-2-[4-(4-piperidinophenyl)-phenoxy]-propionic acid (A), or one of the functional derivatives thereof, with a reducing agent or with a compound of the formula HZ or a functional derivative thereof.

Suitable functional derivatives of Acid A are, primarily: the salts thereof, preferably the alkali metal (Li, Na, K), lead and silver salts; esters thereof, especially the alkyl esters thereof wherein the alkyl group preferably has 1–4 carbon atoms, and the corresponding acid halogenides, preferably the chloride. Other functional derivatives which can be employed are, for example, the nitrile, the azide and the anhydrides derived from A, e.g., the mixed carbonic acid ester anhydrides, and the amides.

The Acid A and the functional derivatives thereof can be reduced, for example with a complex metal hydride, to the corresponding alcohol (I, $R = CH_2OH$). This product is obtained, for example, from the acid or an ester thereof by treatment with $LiAlH_4$, from the azide thereof by treatment with $NaBH_4$, from the acid chloride thereof by treatment with $NaAlH_4$ or $LiAlH_4$, and from the amide thereof by treatment with an alkali metal in a lower alcohol (preferably one having 1–4 carbon atoms), for example, sodium in ethanol. The reduction with a complex hydride is suitably carried out in the presence of an inert solvent, for example an ether, e.g., diethyl ether, THF (tetrahydrofuran), dioxane, 1,2-dimethoxyethane or diglyme. Sodium borohydride can also be employed in an aqueous or aqueous-alcoholic solution. The reaction is advantageously conducted at a temperature of from −80° to +100°, preferably from 20° to the boiling point of the solvent used.

Suitable compounds of the formula HZ are ammonia, mono- and dialkylamines (e.g., wherein the alkyl groups each have 1–4 carbon atoms), ethanolamine, diethanolamine, 2-aminoethanesulfonic acid and the salts thereof, hydrazine and glycine, and also alcohols of the formula $R_3$—OH, viz., 3-pyridylcarbinol, 2-acetamidoethanol, 1-methyl-4-piperidinol and glycerin. Suitable functional derivatives of these compounds are the metal compounds of the above nitrogen bases, e.g., sodium or potassium amide, the metal alcoholates, halogenides and reactive esters derived from the alcohols, e.g., the sodium derivatives $R_3ONa$, 3-pyridylmethyl chloride, 2-acetamidoethyl p-toluenesulfonate, 1-methyl-4-piperidyl iodide and 2,3-dihydroxypropyl bromide. The reaction of Acid A and the functional derivatives thereof takes place in accordance with conventional amidation and esterification methods. The reaction is carried out in the presence or absence of an additional inert solvent. Suitable solvents are, for example, hydrocarbons, e.g., benzene, toluene, and xylene; halogenated hydrocarbons, e.g., methylene chloride, chloroform and 1,2-dichloroethane; ethers, e.g., diethyl ether, THF and dioxane; and amides, e.g., dimethylformamide (DMF), dimethylacetamide, and hexamethylphosphoric triamide (HMPA). It is also possible to utilize an excess of the compound HZ as the solvent. The presence of a catalyst or a dehydrating agent can be advantageous. Suitable catalysts are, for example, inorganic or organic acids, e.g., HCl, HBr, HI, $H_2SO_4$, $H_3PO_4$, trifluoroacetic acid, benzenesulfonic acid, p-toluenesulfonic acid, as well as the acidic ion exchangers.

Suitable dehydration agents are, for example, carbodiimides, e.g., dicyclohexylcarbodiimide. The temperatures used during these reactions are suitably about −20° to 200°.

An especially advantageous embodiment resides in first converting Acid A into its acid chloride, for example with thionyl chloride in benzene, and this acid chloride is reacted, without isolation, with HZ. In this reaction, the same solvent can be employed, or the original solvent can be replaced by another one. In esterification reactions, the addition of a base, such as pyridine, is advantageous.

To produce the esters of Formula I ($R = COOR_3$, $R_3 =$ 3-pyridylmethyl, 2-acetamidoethyl or 1-methyl-4-piperidyl), transesterification methods are suitable. For example, a lower alkyl ester, preferably of 1–4 carbon atoms, of Acid A is heated, together with the alcohol $R_3$—OH to be esterified, to a temperature of about 80° to 200°, preferably 100° to 150°, suitably in the presence of a transesterification catalyst, e.g., sodium. An equilibrium of the two possible esters is produced which is shifted in favor of the desired ester by removing the lower alcohol, e.g., by distillation.

A particularly advantageous method for the preparation of the glycerin ester (Formula I, $R = COOR_3$, $R_3 =$ 2,3-dihydroxypropyl) resides in that the Acid A or the acid chloride thereof is reacted with a glycerin ketal, e.g., 2,3-isopropylidenedioxypropanol, and the ketal group of the thus-obtained product is thereafter split off again under gentle conditions, e.g., with boric acid. In this way, an especially pure product is obtained.

The compounds of Formula I can furthermore be obtained in accordance with conventional methods described in the literature by reacting 4-hydroxy-4'-piperidino-diphenyl (B) with a compound of Formula II, which are novel for the most part and can be produced according to methods known per se, e.g., by reacting 2-bromoisobutyric acid or a derivative thereof with a reducing agent and/or with a compound of the formula HZ. For example, the phenol B can first be converted into a salt, especially a metallic salt, e.g., an alkali metal salt (Li, Na or K salt). The phenol can be reacted, for example, with a reagent forming metallic salts, e.g., an alkali metal (e.g., Na), an alkali-metal hydride or amide (e.g., LiH or NaH, NaNH$_2$ or KNH$_2$), a lower alkali-metal alcoholate (e.g., lithium, sodium or potassium methylate, ethylate or tert.-butylate), an organometal compound derived from a hydrocarbon (e.g., butyllithium, phenyllithium or phenylsodium), a metal hydroxide, carbonate or bicarbonate (e.g., of Li, Na, K or Ca). The salt of B is advantageously prepared in the presence of a solvent or solvent mixture. Suitable solvents are, for example, hydrocarbons, e.g., hexane, benzene, toluene and xylene; ethers, e.g., diethyl ether, diisopropyl ether, THF, dioxane and diethylene glycol dimethyl ether; amides, e.g., DMF; alcohols, e.g., methanol and ethanol; and ketones, e.g., acetone and butanone.

The phenol B or a salt thereof is reacted with a compound of Formula II preferably in the presence of a diluent, e.g., the solvent employed for the preparation of the salt, as such or diluted with or replaced by another solvent. The reaction is normally conducted at a temperature of about −20° to 150°, preferably 20° to 120°.

The metallic salt of phenol B can also be formed in situ in which case, the phenol and the compound II are allowed to react in the presence of a base. An especially preferred method resides in refluxing the compounds B and II (X = Cl or Br) together with an alcoholic (e.g., ethanolic) sodium alcoholate solution for several hours.

It is also possible to react the free phenol B with a hydroxy derivative of Formula II (X = OH), preferably in the presence of a condensation agent. Suitable condensation agents are acidic dehydration catalysts, e.g., mineral acids, for example sulfuric acid and phosphoric acid, p-toluenesulfonyl chloride, arsenic acid, boric acid, NaHSO$_4$ or KHSO$_4$, disubstituted carbonic acid esters, for example, diaryl carbonates (e.g., diphenyl carbonate) and especially dialkyl carbonates (e.g., dimethyl and diethyl carbonate) and carbodiimides (e.g., dicyclohexylcarbodiimide). If an acid serves as the condensation agent, the reaction is advantageously effected in an excess of this acid without the addition of a further solvent, at a temperature of from 0° to 100°, preferably 50° to 60°. However, it is also possible to add a diluent, e.g., benzene, toluene or dioxane. When using a carbonate, the reaction is preferably conducted at a higher temperature, suitably from 100° to about 210°, especially 180° to 200°. A transesterification catalyst such as sodium or potassium carbonate, or an alcoholate (e.g., sodium methylate), can be added, if desired.

A cyclization of the compounds of Formula III is accomplished by heating in the presence or absence of a solvent, optionally in the presence of an acidic or basic catalyst. Compounds of Formula III can be obtained, for example, by reacting a compound of Formula X with 1,5-dibromopentane. Suitable solvents for the cyclization of III are, for example, water, aliphatic alcohols (e.g., methanol, ethanol, isopropanol and n-butanol), glycols (e.g., ethylene glycol), ethers (e.g., diethyl or diisopropyl ether, THF and dioxane), aliphatic hydrocarbons (e.g., petroleum ether and hexane), aromatic hydrocarbons (e.g, benzene, toluene and xylene), and halogenated hydrocarbons (e.g., chloroform, chlorobenzene), nitriles (e.g., acetonitrile), amides (e.g., DMF and dimethylacetamide), sulfoxides (e.g., dimethyl sulfoxide) and mixtures of these solvents. Normally, the cyclization is conducted at temperatures of from 0° to 300°, preferably from room temperature to the boiling point of the solvent employed, which optionally can be raised by the use of pressure (up to 200 atmospheres). The selection of the catalyst is dependent on the type of compound HY to be split off. When Y = Hal, preferred are basic catalysts, e.g., inorganic bases (alkali metal and alkaline earth metal hydroxides, carbonates and alcoholates, e.g., sodium or potassium hydroxide, carbonate and ethylate) and organic bases (e.g., tertiary bases, e.g., triethylamine, pyridine, picolines and quinoline). In contrast thereto, acidic catalysts are advantageous for Y = OH, alkoxy, acyloxy, alkyl- or arylsulfonyloxy, e.g., inorganic acids (e.g., sulfuric acid, polyphosphoric acid, hydrobromic acid and hydrochloric acid) and/or organic acids (e.g., formic, acetic, propionic and p-toluenesulfonic acid), which can simultaneously serve as the solvent if used in excess. Normally, more vigorous conditions are required for the cyclization of these substances. Compounds of Formula III (Y = NH$_2$) split off ammonia during heating, for example when melted, thus forming the desired compounds of Formula I.

In a preferred mode of operation, Compounds III are not isolated, but rather are produced in the nascent state in the presence or absence of an additional solvent (e.g., from 1,5-dibromopentane and a compound of Formula X)

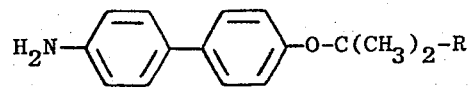

$H_2N$—⟨—⟩—⟨—⟩—$O-C(CH_3)_2-R$        X and are then directly cyclized to compounds of Formula I. The use of a catalyst, e.g., a base, such as NaOH, KOH, sodium carbonate or potassium carbonate, is possible but not absolutely necessary. It is also feasible to utilize an excess of the amino compound X in place of such a base as catalyst.

The reaction of 1,5-dibromopentane with X in a boiling alcohol in the presence of potassium carbonate is particularly advantageous. Compounds of Formula III (Y = Br) are produced as intermediates which are cyclized in situ. Under these conditions, the reaction is complete after about 1–12 hours.

The compounds of Formula I can furthermore be obtained by reacting the halogen compounds IV with the halogen compounds V in the presence of a catalyst, employing Ullmann reaction conditions. In compounds IV and V, Hal preferably is I. Preferred catalysts in this process are heavy metals and heavy metal compounds, especially copper powder or copper(I) oxide. Normally, a large excess, e.g., about 8-10-fold, of these catalysts is employed. The reaction is preferably accomplished at temperatures of from 100° to 350°, preferably 170° to 230°. The reaction is carried out without a solvent or in the presence of a high-boiling solvent, e.g., tetramethylurea. The compounds IV are obtainable, for example, from p-haloanilines and 1,5-dibromopentane. The compounds V can be produced from p-halophenols and the compounds II.

The compounds I can also be obtained by reacting a diazonium compound VI with a phenoxy compound VII under Gomberg reaction conditions. Especially suitable as the diazonium compounds are the corresponding chlorides, which are readily obtainable by diazotization of 1-p-aminophenylpiperidine. During the decomposition of the diazonium chlorides, the reaction is suitably conducted in the presence of a base, e.g., NaOH or sodium acetate, at a temperature of about 0° to 25°, preferably 5° to 10°. An additional inert solvent can be added, for example a halogenated hydrocarbon, e.g., chloroform or carbon tetrachloride. However, it is also possible to employ an excess of Compound VII (when the latter is liquid) as the solvent. In place of the above-mentioned bases, it is also possible to use copper(I) compounds in the presence of ammonia. In this connection, it is advantageous to conduct the reaction at higher temperatures, especially at the boiling temperature of the reaction mixture. In a modification of this reaction, instead of the diazonium compound, N-nitroso-4-piperidinoacetanilide is employed from which, under the reaction conditions, the corresponding diazonium acetate is produced, which is not isolated. In this modification, temperatures of about 30° can be utilized when a basic catalyst, e.g., potassium carbonate, is employed. However, it is also possible to conduct the reaction without catalyst. The starting substances VII can be prepared from phenol and the compounds II.

Compounds of Formula I can also be produced by the reaction of compounds of Formula VIII with compounds of Formula IX. It is possible, for example, to react N-halopiperidines (IX, $X_2$ = Cl or Br), e.g., N-chloropiperidine, or reactive derivatives of N-hydroxypiperidine, e.g., N-hydroxypiperidine-O-sulfonic acid, with compounds of Formula VIII ($X_1$ = H), preferably in the presence of a catalyst, e.g., a metallic salt, for example, iron (II) sulfate, $AlCl_3$, $BF_3$ or $ZnCl_2$, in an inert solvent, e.g., $CS_2$, nitrobenzene, 1,2-dichloroethane, or, when using iron(II) sulfate, in concentrated or aqueous sulfuric acid. Reaction temperatures in this mode of operation are suitably from −20° to +60°, preferably from 0° to 40°. Furthermore, it is possible to react piperidine (IX, $X_2$ = H) with an amino compound of Formula VIII ($X_1$ = $NH_2$), preferably under pressure. In this reaction, either an excess of piperidine is used as the solvent or the reaction is carried out in the presence of an additional inert solvent, as well as an acidic catalyst, e.g., HCl, p-toluenesulfonic acid or a Friedel-Crafts catalyst, e.g., $AlCl_3$, at a temperature of about 50° to about 300°, preferably 150° to 250°. Furthermore, it is possible, for example, to react metal derivatives, especially the sodium derivative of piperidine, with halogen or sulfonic acid derivatives of Formula VIII ($X_1$ = Hal or $SO_3M$), preferably in the presence of an excess of piperidine as the solvent and/or in the presence of an additional inert solvent or suspension agent, e.g., benzene, dioxane, DMF or HMPA at a temperature of about 50° to about 200°, optionally under pressure and/or an inert gas atmosphere. The metal derivatives of piperidine can also be produced in situ, e.g., with NaH or $NaNH_2$. The starting compounds of Formula VIII are obtainable, for example, by reacting 4-hydroxy-4'-$X_1$-diphenyl with compounds of Formula II. The starting compounds of Formula IX are known or can be prepared in accordance with standard methods analogously to the known compounds.

A basic compound of Formula I can be converted with acid into the associated acid addition salt. Suitable for this reaction are those acids yielding physiologically acceptable salts. Suitable are both organic and inorganic acids, e.g., aliphatic, alicyclic, araliphatic, aromatic or heterocyclic mono- or polybasic carboxylic or sulfonic acids, e.g., formic acid, acetic acid, propionic acid, pivalic acid, diethylacetic acid, malonic acid, succinic acid, pimelic acid, fumaric acid, maleic acid, lactic acid, tartaric acid, malic acid, aminocarboxylic acids, sulfamic acid, benzoic acid, salicylic acid, 2-phenylpropionic acid, citric acid, gluconic acid, ascorbic acid, nicotinic acid, isonicotinic acid, methanesulfonic acid, ethanedisulfonic acid, 2-hydroxyethanesulfonic acid, p-toluenesulfonic acid, naphthalene-mono- and -disulfonic acids, sulfuric acid, nitric acid, hydrohalic acids, e.g., hydrochloric acid or hydrobromic acid, or phosphoric acids, e.g., orthophosphoric acid.

The acidic compounds of Formula I can be converted, by reaction with a base, into one of the physiologically acceptable metallic and/or ammonium salts thereof. Especially suitable salts are the sodium, potassium, magnesium, calcium and ammonium and substituted ammonium salts.

Conversely, compounds of Formula I can be liberated from the acid addition salts thereof by treatment with strong bases and/or from the metal and ammonium salts thereof by treatment with acids.

The compounds of Formula I and the physiologically acceptable salts thereof can be utilized in admixture with solid, liquid and/or semiliquid excipients as medicinal agents in the human or veterinary medicine. Suitable carriers are those organic or inorganic substances suitable for parenteral, enteral or topical application and which do not react with the novel compounds, such as, for example, water, vegetable oils, benzyl alcohols, polyethylene glycols, gelatin, lactose, amylose, magnesium stearate, talc, vaseline, cholesterol. Especially suitable for parenteral application are solutions, preferably oily or aqueous solutions, as well as suspensions, emulsions or implants. Suitable for enteral application are tablets, dragees, capsules, syrups, elixirs or suppositories, and for topical administration, ointments, creams or powders. The above-mentioned preparations can optionally be sterilized or can contain auxiliary agents, such as lubricants, preservatives, stabilizers or wetting agents, emulsifiers, salts to influence the osmotic pressure, buffers, coloring, flavoring and/or aromatic substances.

Compounds of this invention are preferably administered in dosages of 10 to 1000 mg. per dosage unit.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

The temperatures are indicated herein in degrees Celsius.

EXAMPLE 1

A solution of 14.7 g. of the ethyl ester of 2-methyl-2-[4-(4-piperidinophenyl)-phenoxy]-propionic acid in 80 ml. of absolute THF is added dropwise to a suspension of 1.5 g. of LiAlH$_4$ in 120 ml. of absolute THF. The mixture is refluxed for 3 hours under agitation, then combined with a mixture of 10 ml. of ethyl acetate, 5 ml. of water, and 25 ml. of THF and then with 15 ml. of 32% strength sodium hydroxide solution; the mixture is filtered, the filtrate is dried, the solvent is removed, and the thus-obtained product is 2-methyl-2-[4-(4-piperidinophenyl)-phenoxy]-propanol, m.p. 158°–160°.

EXAMPLE 2

A solution of 3.39 g. of 2-methyl-2-[4-(4-piperidinophenyl)-phenoxy]-propionic acid in 50 ml. of absolute benzene is combined with 1.1 g. of thionyl chloride and refluxed for 2 hours. The mixture is concentrated by evaporation, the residue is dissolved in 10 ml. of dioxane, and the solution is added dropwise under stirring to 20 ml. of 25% strength ammonia solution. During this step, 2-methyl-2-[4-(4-piperidinophenyl)-phenoxy]-propionic acid amide is precipitated, m.p. 210°–212° (THF/methanol).

Analogously, the following final products are obtained with methylamine, ethylamine, propylamine, isopropylamine, n-butylamine, isobutylamine, dimethylamine, diethylamine, ethanolamine, diethanolamine, 2-aminoethanesulfonic acid potassium salt, hydrazine hydrate, and glycine, respectively:

2-methyl-2-[4-(4-piperidinophenyl)-phenoxy]-propionic acid methylamide;
2-methyl-2-[4-(4-piperidinophenyl)-phenoxy]-propionic acid ethylamide;
2-methyl-2-[4-(4-piperidinophenyl)-phenoxy]-propionic acid n-propylamide;
2-methyl-2-[4-(4-piperidinophenyl)-phenoxy]-propionic acid isopropylamide, m.p. 132°–134°;
2-methyl-2-[4-(4-piperidinophenyl)-phenoxy]-propionic acid n-butylamide;
2-methyl-2-[4-(4-piperidinophenyl)-phenoxy]-propionic acid isobutylamide;
2-methyl-2-[4-(4-piperidinophenyl)-phenoxy]-propionic acid dimethylamide;
2-methyl-2-[4-(4-piperidinophenyl)-phenoxy]-propionic acid diethylamide, m.p. 100°–102°;
2-methyl-2-[4-(4-piperidinophenyl)-phenoxy]-propionic acid 2-hydroxyethylamide, m.p. 140°–141°;
2-methyl-2-[4-(4-piperidinophenyl)-phenoxy]-propionic acid N,N-bis-(2-hydroxyethyl)-amide, m.p. 160°–161°;
2-methyl-2-[4-(4-piperidinophenyl)-phenoxy]-propionic acid 2-hydroxysulfonylethylamide, potassium salt, m.p. 260°–265°;
2-methyl-2-[4-(4-piperidinophenyl)-phenoxy]-propionic acid hydrazide, m.p. 157°–159°;
2-methyl-2-[4-(4-piperidinophenyl)-phenoxy]-propionic acid N-carboxymethylamide.

EXAMPLE 3

A mixture of 3.39 g. of 2-methyl-2-[4-(4-piperidinophenyl)-phenoxy]-propionic acid, 3.6 g. of pyridyl-3-methanol, 2.27 g. of dicyclohexylcarbodiimide, and 35 ml. of absolute THF is allowed to stand overnight at 20°. The mixture is then filtered, the filtrate is mixed with water and extracted with ethyl acetate. After drying and evaporation, the crude product is dissolved in chloroform and filtered over silica gel, thus obtaining the (3-pyridylmethyl) ester of 2-methyl-2-[4-(4-piperidinophenyl)-phenoxy]-propionic acid, m.p. 111°–113°.

Analogously, the following products are obtained with N-(2-hydroxyethyl)-acetamide and 1-methyl-4-hydroxypiperidine, respectively:

the (2-acetamidoethyl) ester of 2-methyl-2-[4-(4-piperidinophenyl)-phenoxy]-propionic acid, m.p. 120°–122° and
the (1-methyl-4-piperidyl) ester of 2-methyl-2-[4-(4-piperidinophenyl)-phenoxy]-propionic acid, m.p. 78°–82°.

EXAMPLE 4

A mixture of 3.39 g. of 2-methyl-2-[4-(4-piperidinophenyl)-phenoxy]-propionic acid, 1.1 ml. of thionyl chloride, and 50 ml. of benzene is refluxed for 2 hours. The mixture is evaporated, the residue is suspended in 15 ml. of DMF, and this suspension is added to a solution of 1.03 g. of N-(2-hydroxyethyl)-acetamide in 3.2 g. of pyridine. The mixture is stirred for 24 hours at 20°, then poured into water and extracted with chloroform. After drying, evaporation, dissolution of the crude product in chloroform/ethyl acetate, 24:1, and filtration over silica gel, the (2-acetamidoethyl) ester of 2-methyl-2-[4-(4-piperidinophenyl)-phenoxy]-propionic acid is produced, m.p. 120°–122°.

EXAMPLE 5

A mixture of 6 g. of the ethyl ester of 2-methyl-2-[4-(4-piperidinophenyl)-phenoxy]-propionic acid, 30 ml. of dimethylacetamide, and 10 ml. of 80% hydrazine hydrate is heated for 8 hours to 60°. The mixture is allowed to cool, poured on water, filtered, washed with water, dried, and the thus-obtained product is 2-methyl-2-[4-(4-piperidinophenyl)-phenoxy]-propionic acid hydrazide, m.p. 157°–159°.

EXAMPLE 6

A solution is made from 1.5 g. of sodium and 140 ml. of ethanol; 22 g. of 2-methyl-2-[4-(4-piperidinophenyl)-phenoxy]-propionic acid is added thereto, and then 180 ml. of HMPA is introduced. The reaction mixture is freed of ethanol by gradual distillation at a bath temperature of 130°. After adding 5.2 ml. of 3-chloropropanediol, the temperature is raised to 160° and maintained for 7 hours. The mixture is then poured on ice water, extracted with ether, dried, and evaporated, thus obtaining the (2,3-dihydroxypropyl) ester of 2-methyl-2-[4-(4-piperidinophenyl)-phenoxy]-propionic acid, m.p. 94°–96°.

Analogously, the corresponding compounds of Formula 1 are obtained with 3-chloromethylpyridine, 2-acetamidoethyl chloride, and 1-methyl-4-chloropiperidine, respectively.

EXAMPLE 7

A solution is prepared from 2.3 g. of sodium and 100 ml. of absolute alcohol; 25.3 g. of 4-hydroxy-4'-piperidino-diphenyl and 16.6 g. of 2-bromoisobutyramide are added to the reaction mixture and the latter refluxed for 3 hours. The reaction mixture is then evaporated, the residue is mixed with water, and the thus-obtained suspension is extracted with ether. The ether solution is washed with dilute sodium hydroxide solution and water, dried, and evaporated, thus producing 2-methyl-2-[4-(4-piperidinophenyl)-phenoxy]-propionic acid amide, m.p. 210°–212°.

Analogously, the corresponding compounds of Formula 1 are obtained with 2-bromo-2-methylpropanol; 2-bromoisobutyric acid methylamide, ethylamide, n-propylamide, isopropylamide, n-butylamide, isobutylamide, dimethylamide, diethylamide, 2-hydroxyethylamide, N,N-bis-(2-hydroxyethyl)-amide, 2-hydroxysulfonylethylamide (sodium salt), hydrazide, N-carboxymethylamide, 3-pyridylmethyl ester, 2-acetamidoethyl ester, 1-methyl-4-piperidyl ester, and 2,3-dihydroxypropyl ester, respectively; or with the corresponding chlorine compounds.

EXAMPLE 8

25.3 g. Of 4-hydroxy-4'-piperidino-diphenyl is dissolved in 200 ml. of acetone. Under agitation, 4 g. of NaOH is added thereto, and then, under stirring and boiling, 12.15 g. of 2-chloroisobutyramide in 60 ml. of acetone is added dropwise to the mixture. The latter is agitated for 1 hour at 56° and allowed to stand for 24 hours. The acetone is then distilled off, the mixture worked up with water and ether, and the product is 2-methyl-2-[4-(4-piperidinophenyl)-phenoxy]-propionic acid amide, m.p. 210°–212°.

Analogously, the corresponding compounds of Formula 1 are obtained with 2-chloro-2-methylpropanol; 2-chloroisobutyric acid methylamide, ethylamide, n-propylamide, isopropylamide, n-butylamide, isobutylamide, dimethylamide, diethylamide, 2-hydroxyethylamide, N,N-bis-(2-hydroxyethyl)-amide, 2-hydroxysulfonylethylamide (sodium salt), hydrazide, N-carboxymethylamide, 3-pyridylmethyl ester, 2-acetamidoethyl ester, 1-methyl-4-piperidyl ester, and 2,3-dihydroxypropyl ester; or with the corresponding bromine compounds.

EXAMPLE 9

To a mixture of 25.3 g. of 4-hydroxy-4'-piperidinodiphenyl and 12 g. of 2-hydroxyisobutyramide is added 15 g. of sulfuric acid, and the reaction mixture is agitated for 2 hours at 50°–60°. After cooling, the mixture is combined with water, dilute sodium hydroxide solution is added to pH 8, and the mixture is extracted with ether, dried, and evaporated, thus producing 2-methyl-2-[4-(4-piperidinophenyl)-phenoxy]-propionic acid amide, m.p. 210°–212°.

EXAMPLE 10

23 g. of 1,5-dibromopentane, 25.7 g. of 2-methyl-2-[4-(4-aminophenyl)-phenoxy]-propanol (obtainable by reaction of 4-hydroxy-4'-nitro-diphenyl with 2-bromo-2-methylpropanol to 2-methyl-2-[4-(4-nitrophenyl)-phenoxy]-propanol and reduction), and 27 g. of potassium carbonate are refluxed in 400 ml. of n-butanol for 12 hours. 2-Methyl-2-[4-(p-5-bromopentylaminophenyl)-phenoxy]-propanol is formed as the intermediate, which is not isolated. Then, the solvent is distilled off, the residue mixed with water and extracted with ethyl acetate. After drying and evaporation, 2-methyl-2-[4-(4-piperidinophenyl)-phenoxy]-propanol is obtained, m.p. 158°–160°.

Analogously, via the corresponding intermediates, the corresponding compounds of Formula 1 are produced from 2-methyl-2-[4-(4-aminophenyl)-phenoxy]-propionic acid amide, methylamide, ethylamide, n-propylamide, isopropylamide, n-butylamide, isobutylamide, dimethylamide, diethylamide, 2-hydroxyethylamide, N,N-bis-(2-hydroxyethyl)-amide, 2-hydroxysulfonylethylamide (potassium salt), hydrazide, N-carboxymethylamide, 3-pyridylmethyl ester, 2-acetamidoethyl ester, 1-methyl-4-piperidyl ester, and 2,3-dihydroxypropyl ester, respectively.

EXAMPLE 11

A mixture of 2.87 g. of 1-p-iodophenylpiperidine (obtainable from p-iodoaniline and 1,5-dibromopentane) and 3.61 g. of 2-methyl-2-p-iodophenoxypropionic acid diethylamide (obtainable from p-iodophenol and 2-bromoisobutyric acid diethylamide) is heated with 6.5 g. of copper powder for 3 hours to 220°. The mixture is then cooled off, worked up with water and ether, the thus-obtained product being 2-methyl-2-[4-(4-piperidinophenyl)-phenoxy]-propionic acid diethylamide, m.p. 100°–102°.

EXAMPLE 12

A mixture of 2.87 g. of 1-p-iodophenylpiperidine, 3.61 g. of 2-methyl-2-p-iodophenoxypropionic acid diethylamide, 11.5 g. of copper(I) oxide, and 50 ml. of tetramethylurea is heated for 12 hours to 180°. The mixture is then cooled off and worked up with water and ether, thus producing 2-methyl-2-[4-(4-piperidinophenyl)-phenoxy]-propionic acid diethylamide, m.p. 100°–102°.

EXAMPLE 13

At 5°, 33.2 g. of 2-methyl-2-phenoxy-1-propanol (obtainable from phenol and 2-bromo-2-methyl-1-propanol) is added to a diazonium salt solution formed by diazotizing 17.6 g. of 1-p-aminophenylpiperidine (producible by reacting p-nitroaniline with 1,5-dibromopentane and subsequent reduction). Then, under agitation, 35% strength NaOH solution is added dropwise until the reaction is weakly alkaline. The mixture is then further stirred for 12 hours at 10° and thereafter briefly heated to 70°. After cooling, the organic phase is separated, dried, the excess 2-methyl-2-phenoxy-1-propanol is distilled off, and the product thus obtained is 2-methyl-2-[4-(4-piperidinophenyl)-phenoxy]-propanol, m.p. 158°–160°.

EXAMPLE 14

2.47 g. of N-nitroso-4-piperidinoacetanilide (producible by introducing $N_2O_3$ into an ice-cold solution of 4-piperidinoacetanilide in acetic acid) is gradually introduced into ice cooling into 33 g. of 2-methyl-2-phenoxy-1-propanol. The mixture is stirred for 2 days at 20°. After the excess 2-methyl-2-phenoxy-1-propanol has been distilled off, 2-methyl-2-[4-(4-piperidinophenyl)-phenoxy]-propanol remains, m.p. 158°–160°.

EXAMPLE 15

Under agitation, a solution of 12 g. of N-chloropiperidine in 15 ml. of concentrated sulfuric acid is added dropwise within 10 minutes to a mixture of 24.2 g. of 2-methyl-2-(4-phenylphenoxy)-propanol (obtainable from 4-hydroxy-diphenyl and 2-bromo-2-methylpropanol), 7 g. of iron(II) sulfate heptahydrate, 8 ml. of concentrated sulfuric acid, and 3 ml. of water. The mixture is agitated for 15 minutes at 20°, then poured on ice water, washed with ether, made alkaline with sodium hydroxide solution, and extracted with chloroform. From the extract, after evaporation, one obtains 2-methyl-2-[4-(4-piperidinophenyl)-phenoxy]-propanol, m.p. 158°–160°.

EXAMPLE 16

19 ml. Of piperidine and 3.9 g. of $NaNH_2$ are refluxed for 1 hour under agitation and while introducing nitrogen. Thereafter, 34.4 g. of the sodium salt of 2-methyl-2-[4-(4-sulfophenyl)-phenoxy]-propanol [obtainable by sulfonation of 2-methyl-2-(4-phenylphenoxy)-propanol] and another 19 ml. of piperidine are added thereto, and the mixture is refluxed under agitaion for 12 hours. After cooling, the mixture is worked up with water and ether, thus producing 2-methyl-2-[4-(4-piperidinophenyl)-phenoxy]-propanol, m.p. 158°–160°.

EXAMPLE 17

A mixture of 29.35 g. of 2-methyl-2-[4-(4-aminophenyl)-phenoxy]-propanol hydrochloride, 15 ml. of piperidine, and 1 g. of $AlCl_3$ is heated in an autoclave for 48 hours to 200°. After cooling and working up the mixture as usual, 2-methyl-2-[4-(4-piperidinophenyl)-pehnoxy]-propanol is obtained, m.p. 158°–160°.

EXAMPLE 18

A mixture of 39 g. of 2-methyl-2-[4-(4-bromophenyl)-phenoxy]-propionic acid diethylamide [obtainable by bromination of 2-methyl-2-(4-phenylphenoxy)-propionic acid diethylamide], 8.5 g. of piperidine, 2.4 g. of NaH, and 60 ml. of HMPA is agitated overnight at 150°. After cooling and the usual working-up operation, 2-methyl-2-[4-(4-piperidinophenyl)-phenoxy]-propionic acid diethylamide is obtained, m.p. 100°–102°.

EXAMPLE 19

33.9 g. Of 2-methyl-2-[4-(4-piperidinophenyl)-phenoxy]-propionic acid is refluxed for 2 hours with 23.8 g. of thionyl chloride in 500 ml. of benzene and then evaporated. The residue is cooled to 5°, combined with 23.7 g. of pyridine and 25 ml. of 2,3-isopropylidenedioxypropanol, and the mixture is agitated for 18 hours at 20°, then poured on water, and extracted with methylene chloride. The reaction mixture is worked up, and the thus-obtained 2,3-isopropylidenedioxypropyl ester is dissolved in 200 ml. of trimethylborate; 18 g. of boric acid is added thereto, and the mixture agitated for 1 hour at 90°. After evaporating and working up with water and methylene chloride, pure, isomer-free (2,3-dihydroxypropyl) ester of 2-methyl-2-[4-(4-piperidinophenyl)-phenoxy]-propionic acid is obtained, m.p. 94°–96°.

EXAMPLE 20

30 g. Of 1-methyl-4-hydroxpiperidine is heated with 0.2 g. of sodium until dissolved, and at 100°, 36.7 g. of the ethyl ester of 2-methyl-2-[4-(4-piperidinophenyl)-phenoxy]-propionic acid is added thereto, whereafter the mixture is heated for 14 hours to 150°; at 100–150 torr [mm. Hg], the thus-formed ethanol is distilled off via a small column. The mixture is cooled, and toluene, dilute acetic acid, and concentrated hydrochloric acid are added successively thereto. The mixture is filtered, and the acidic phase is clarified with carbon. After the addition of methylene chloride, the mixture is made alkaline, is separated, washed with water, and evaporated, thus obtaining the (1-methyl-4-piperidyl) ester of 2-methyl-2-[4-(4-piperidinophenyl)-phenoxy]-propionic acid in two modifications, m.p. 91°–91.5° and m.p. 110°–112°.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scop thereof, can make various changes and modifications of the invention to adapt it to various usages and conditions.

What is claimed is:

1. A compound of the formula

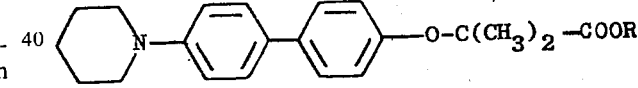

wherein R is 1-methyl-4-piperidyl, or a physiologically acceptable salt thereof.

2. A compound of claim 1, 2-methyl-2-[4-(4-piperindinophenyl)-phenoxy]-propionic acid 1-methyl-4-piperidyl ester.

* * * * *